United States Patent [19]

Robin

[11] Patent Number: 4,828,753

[45] Date of Patent: May 9, 1989

[54] STORAGE-STABLE ORGANIC SOLUTIONS OF POLYISOCYANATES

[75] Inventor: Jean Robin, Lyons, France

[73] Assignee: Rhone-Poulenc Specialities Chimiques, Courbevoie, France

[21] Appl. No.: 865,420

[22] Filed: May 21, 1986

[30] Foreign Application Priority Data

May 21, 1985 [FR] France ................... 85 07817

[51] Int. Cl.$^4$ ............................. C09K 3/00
[52] U.S. Cl. .................................. 252/182.2
[58] Field of Search ................. 252/182, 182.2

[56] References Cited

U.S. PATENT DOCUMENTS

| 3,376,230 | 4/1968 | McShane ................... 252/182.2 |
| 4,344,855 | 8/1982 | Schäfer et al. ................. 252/182 |
| 4,357,255 | 11/1982 | Stemmler et al. ............. 252/182 |
| 4,442,279 | 4/1984 | Fauss et al. ................... 252/182 |
| 4,442,280 | 4/1984 | Grögler .......................... 252/182 |
| 4,581,432 | 4/1986 | Blum et al. ................... 252/182 |
| 4,595,712 | 6/1986 | Laumain ....................... 252/182 |

FOREIGN PATENT DOCUMENTS 1141708 1/1969 United Kingdom .

Primary Examiner—Edward A. Miller
Attorney, Agent, or Firm—Burns, Doane, Swecker & Mathis

[57] ABSTRACT

Inert organic solvent solutions of polyisocyanates, well adopted as coating compositions, are storage-stabilized, e.g., against the formation of precipitates, by incorporating therein an effective amount of at least one organostannic compound which is soluble in the organic solvent.

7 Claims, No Drawings

STORAGE-STABLE ORGANIC SOLUTIONS OF POLYISOCYANATES

BACKGROUND OF THE INVENTION

1. Field of the Invention:

The present invention relates to the stabilization of solutions of polyisocyanates in organic solvents against the formation of precipitates during storage.

2. Description of the Prior Art:

Because of their chemical and mechanical properties, polyurethane-based coatings are being widely used in this art as paints, lacquers and varnishes for various substrates such as metals, wood, concrete and polymers. In most cases, these polyurethane coatings are produced by the reaction, on a given substrate, of a polyhydroxylated compound (for example, polyols, polyhydroxylated polyethers or polyhydroxylated polyesters) with a compound containing a plurality of isocyanate groups, in the presence of adjuvants intended to promote the reaction and the hardening of the resultant film. The reactivity of the compounds containing free hydroxyl groups with the compounds containing free isocyanate groups necessitates that the contact between the two reactants take place only shortly prior to application, for example, in the mixing chamber of spraying equipment into which they are separately charged.

Thus, under these conditions, the formation of the polyurethane coating entails the use of two separate components, which accounts for such compositions being designated as two-component or two-part coating compositions (varnishes, paints or lacquers) in the art. In general, one of the two components contains the polyhydroxylated compound, to which various adjuvants may be added, such as pigments, thickeners, flow-improvers, stabilizers (for example, UV stabilizers) and, if appropriate, a polyaddition catalyst, and the other component is a solution of one or more compounds containing free isocyanate groups, in an organic solvent or a mixture of organic solvents which is intended to facilitate the use of the polyisocyanate component and its mixing with the polyhydroxylated component. The solvents used for this purpose are compounds which are liquid under conditions of normal pressure and temperature and which must be free from functional groups capable of reacting with isocyanate groups, and especially devoid of functional groups containing active Zerewitinoff hydrogen atoms, such as amino, hydroxyl, mercaptan and carboxyl groups. For these solutions to be stable, it is also important that the solvents be free from water, a condition which is especially difficult to meet on an industrial scale without having to resort to costly means for removing the last traces of water. Furthermore, whatever the efforts made to remove water, it is difficult to maintain the solvents in anhydrous state. In fact, water may be introduced adventitiously, notably by atmospheric water vapor in the case of hydrophilic solvents. It too has been found that the presence of trace amounts of water in organic solvents for polyisocyanates causes the formation of precipitates while they are in storage, which is harmful to their appearance and to their ultimate use and can spoil the appearance of the final coating. Consequently, serious need exists in this art for means to avoid, on the one hand, the use of costly processes for removing trace amounts of water from the solvents employed to produce organic solutions of polyisocyanates and, on the other hand, the formation of precipitates in these solutions containing trace amounts of water.

SUMMARY OF THE INVENTION

Accordingly, a major object of the present invention is the provision of a novel class of organic solvent solutions of polyisocyanates, which solvent solutions/compositions are storage-stable aginst the formation of precipitates therein and which otherwise are conspicuously devoid of the aforesaid disadvantages and drawbacks to date characterizing the state of this art.

Briefly, the present invention features the stabilization of solutions of polyisocyanates in inert organic solvents, against the formation of precipitates, by incorporating therein an effective precipitation-preventing amount of at least one organostannic compound which is soluble in the organic solvent.

It has thus unexpectedly and surprisingly been found that the presence of an organostannic derivative which is soluble in the organic solution of polyisocyanate inhibits the formation of precipitates during storage.

DETAILED DESCRIPTION OF THE PREFERRED EMBODIMENTS OF THE INVENTION

More particularly according to the present invention, the subject organostannic compounds, which are soluble in those solvents typically employed for dissolving the polyisocyanate component of the polyurethane coating compositions, advantageously have the general formula:

$$(R)_m\text{—Sn}(X)_{4-m} \qquad (I)$$

in which:

$m = 2$ or 3;

R is a hydrocarbon radical containing from 1 to 30 carbon atoms, optionally substituted by a halogen atom or a functional group which is inert toward isocyanate groups, the various radicals R being capable of being identical or different;

X is a halogen atom, an acyloxy radical, a sulfonyloxy radical, an oxygen-containing inorganic acid radical, a radical of the formula R—Z— in which R is as defined above and Z is an oxygen or sulfur atom or a radical of the formula —Z—Sn(R)$_3$, in which Z and R are as defined above.

In said formula (I), R is preferably an alkyl radical containing from 1 to 30 carbon atoms and preferably from 1 to 20 carbon atoms, such as methyl, ethyl, propyl, isopropyl, n-butyl, isobutyl, tert-butyl, n-pentyl, isoamyl, n-hexyl, n-heptyl, 2-ethylhexyl, n-octyl, decyl, dodecyl or octadecyl; an alicyclic radical containing from 5 to 15 carbon atoms and preferably from 5 to 12 carbon atoms, such as cyclopentyl, cyclohexyl, 2-methylcyclohexyl, 4-methylcyclohexyl, 2,4-dimethylcyclohexyl or cyclododecyl; an aryl radical such as phenyl, naphthyl, toluyl or xylyl; or an arylalkyl radical containing from 1 to 10 carbon atoms in the alkyl moiety, such as benzyl, alpha-phenylethyl, or β-phenylethyl. These hydrocarbon radicals may be substituted by one or more halogen atoms such as chlorine, bromine or fluorine and/or by inert functional groups such as alkoxy (methoxy, ethoxy, propoxy or butoxy); carbonyloxyalkyl (carbonyloxymethyl, carbonyloxyethyl); nitro; or acyl (acetyl, propionyl or benzoyl);

X is preferably a chlorine, bromine, fluorine or iodine atom; an acyloxy radical of the formula R$_1$—COO in which $R_1$ is an alkyl, cycloalkyl, aryl, or arylalkyl radical such as those defined under R; an acyloxy radical of the general formula:

$$(R_2OOC)_p—R_3—COO—$$

in which:

$R_2$ is a lower alkyl radical or a radical $(R)_3Sn-$, with R being as defined above;

p is 1 to 2;

$R_3$ is a saturated aliphatic, saturated alicyclic, or di- or trivalent aromatic hydrocarbon radical such as tetramethylene, pentamethylene, hexamethylene, dodecamethylene, o-phenylene, meta-phenylene or para-phenylene;

or X is a sulfonyloxy radical $R_1$—$SO_3$—($R_1$ being as defined above); a radical of the formula:

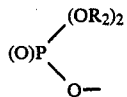

in which $R_2$ is as defined above, the two radicals $R_2$ being capable of being identical or different; or a radical of the formula:

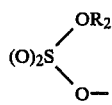

in which $R_2$ is as defined above.

The organostannic compounds which are suitable for use according to the present invention may be selected from among those noted in R.K. Ingham et al, Chem. Rev., 60, pages 459 to 539 (1960). Exemplary of such organostannic compounds, representative are tribenzyltin chloride, tribenzyltin fluoride, tributyltin chloride, tricyclohexyltin bromide, triisobutyltin chloride, trioctyltin bromide, triphenyltin chloride, tris(paracarbomethoxyphenyl)tin chloride, tris(p-chlorophenyl)tin chloride, bis(2-carbomethoxyethyl)-propyltin chloride, butyldi-cyclohexyltin bromide, decyldimethyltin bromide, dibutylphenyltin chloride, dimethyloctyltin bromide, phenyldioctyltin bromide, diphenyloctyltin chloride, dodecyldiethyltin chloride, dichlorodibenzyltin, dichlorodibutyltin, dichlorodicyclohexyltin, dichlorodiphenyltin, dichlorodioctyltin, chlorobromodiphenyltin, dichloromethyloctyltin, methoxytributyltin, methoxytrioctyltin, butoxytributyltin, dibutyldiphenoxytin, (n-octylthio)triethyltin, (tert-butylthio)triethyltin, bis(2-ethylhexyl)tin dilaurate, dibutyldodecyltin laurate, dibutyltin adipate, dibutyltin diacetate, bis(tributyltin) phthalate, dodecyldiethyltin acetate, bis(triethyltin) sulfate, diisoamyltin disulfate, dibutyltin bis(p-toluenesulfonate), dibutyldilauryltin diphosphate, dibutyl(dodecylthio)tin laurate, bis(dibutylmethoxytin) phthalate, triethyltin and tributyltin oxide, bis(tributyltin) sulfide and bis(triphenyltin) sulfide.

The amount of organostannic compounds, expressed as a percentage of the weight of the polyisocyanate can vary over wide limits, depending upon the nature of the polyisocyanate, that of the solvent, and that of the organostannic compound. The minimum amount which is necessary to inhibit the formation of the precipitates may be determined by means of simple tests. There is no critical upper limit, but there is generally no advantage in using an amount of organostannic compound which represents more than 5% of the weight of the polyisocyanate. Amounts ranging from $1.10^{-4}$ to 2%, and preferably from $1.10^{-3}$ to 1% of the weight of the polyisocyanate are typically suitable.

The polyisocyanate solutions which can be stabilized according to the present invention are those which are typically employed in two-component coating compositions. The solvents are those which are normally employed in compositions of this type. Exemplary of such solvents are those noted in general texts on the subject of polyurethane coatings, such as J. H. Saunders et al Polyurethanes — Chemistry and Technology: "I. Chemistry", Interscience Publishers (1963) and "II. Technology", Interscience Publishers (1964), and K. Weigel Polyurethan Lacke, published by Holzverlag (1966). The following solvents are representative: esters such as ethyl acetate, butyl acetate, amyl acetate, ethylene glycol monomethyl ether acetate, ethylene glycol acetate and methoxybutyl acetate; ketones such as cyclohexanone, methyl isobutyl ketone and methyl ethyl ketone; halogenated hydrocarbons such as methylene chloride and trichloroethylene; aromatic hydrocarbons such as benzene, toluene, xylenes and their halogenated derivatives; ethers such as methyl isopropyl ether, methyl isobutyl ether and dimethyl or diethyl ethers of mono- and diethylene glycols. It is of course also within the ambit of the present invention to use solutions of polyisocyanates in mixtures of two or more of the aforementioned solvents. It is preferred to use solutions comprised of hydrophilic solvents.

The polyisocyanates in the organic solutions are those which are employed or can be employed in coating compositions. Examples of such polyisocyanates are noted in the texts by Saunders et al and by Weigel, referred to above. More specifically, and without limitation, representative are aromatic diisocyanates such as toluene diisocyanate (TDI), bis(isocyanatophenyl)methane, bis(3-methyl-4-isocyanatophenyl)methane, xylylene diisocyanates, 1,5-naphthalene diisocyanate; aliphatic or alicyclic diisocyanates such as pentamethylene diisocyanate, hexamethylene diisocyanate, octamethylene diisocyanate, 1,4-diisocyanatocyclohexane, bis(4-isocyanatocyclohexyl)methane, and isophorone diisocyanate; polyisocyanates having a biuret structure, obtained by reaction of an aliphatic or predominantly aliphatic diisocyanate with water or with a compound containing active Zerewitinoff hydrogen (exemplary of such polyisocyanates having a biuret structure are those derived from hexamethylene diisocyanate and from 1,4-diisocyanatocyclohexane); polyisocyanates having an isocyanurate structure which are obtained by catalytic cyclotrimerization of aliphatic, alicyclic or aromatic polyisocyanates (exemplary are the polyisocyanatopolyisocyanurates which are obtained by cyclotrimerization of di-or polyisocyanates such as described in European Patent No. 0,057,653); and "adducts" are suitable which contain free isocyanate groups and which are obtained by condensation of an excess of a di- or polyisocyanate with one or more compounds containing active hydrogens, such as a polyol: glycols (ethylene glycol, propylene glycol); polyols (trimethylolpropane); or an ether diol (diethylene glycol or dipropylene glycol) nonpolymeric in nature (compounds having a molecular weight which is insufficient to enable them to be formed into films).

From a practical point of view, the stabilization of the organic polyisocyanate compositions is effected simply by adding the organostannic compound either to the solvent prior to the dissolution of the polyisocyanate therein, or to the existing polyisocyanate solution. Addition of an effective amount of an organostannic compound to the polyisocyanate before it is dissolved is not without the scope of the invention.

In order to further illustrate the present invention and the advantages thereof, the following specific examples are given, it being understood that same are intended only as illustrative and in nowise limitative.

EXAMPLES 1 to 10

The following materials were charged into 100-ml flasks:
(i) 12 g of an isocyanurate trimer of hexamethylene diisocyanate, free from the latter,
(ii) 14 g of ethyl acetate,
(iii) 14 g of xylene, and
(iv) 500 parts per million by weight, based on the polyisocyanate, of the organostannic compounds listed below.

The flasks were stoppered and stored at 60° C. together with a control flask which did not contain any tin compound. The flasks were stored for three months under these conditions and were examined at 10-day intervals. It was found that on the tenth day the solution which did not contain an organostannic compound was cloudy, whereas after three months the contents of the other flasks remained clear. The following organostannic compounds were tested:
Example 1: dibutyltin oxide;
Example 2: tributyltin chloride;
Example 3: tributyltin benzoate;
Example 4: tributyltin diethyl phosphate;
Example 5: tris(tributyltin) phosphate;
Example 6: lauryldiethyltin acetate;
Example 7: triethyltin laurate;
Example 8: methoxytributyltin;
Example 9: methoxydibutyltin acetate;
Example 10: triethyl(isobutylthio)tin.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A storage-stable composition of matter, consisting essentially of comprising a solution of a polyisocyanate in an inert organic solvent therefor, and a precipitate-inhibiting amount of at least one organostannic compound, which is soluble in said organic solvent, and having the general formula:

$$(R)_m-Sn(X)_{4-m} \quad (I)$$

in which m is 3; each R, which may be identical or different, is a hydrocarbon radical containing from 1 to 30 carbon atoms, or a substituted such radical bearing at least one halo or isocyanato-inert substituent; and x is a halogen atom, an acyloxy radical, a sulfonyloxy radical, an oxygen-containing inorganic acid radical, a radical of the formula R—Z— in which R is as defined above and Z is an oxygen or sulfur atom, or a radical of the formula —Z—Sn(R)$_3$ in which Z and R are as defined above.

2. The storage-stable composition as defined by claim 1 wherein said at least one organostannic compound having the general formula (I), R is an alkyl radical containing from 1 to 30 carbon atoms, an alicyclic radical containing from 5 to 15 carbon atoms, an aryl radical, an arylalkyl radical containing from 1 to 10 carbon atoms, or substituted such radicals bearing at least on halo, alkoxy, carbonyloxyalkyl, nitro or acyl substituent; X is a halogen atom, an acyloxy radical of the formula R$_1$—COO in which R$_1$ is an alkyl, cycloalkyl, aryl or arylalkyl radical as defined under R, an acyloxy radical of the formula:

$$(R_2COO)_p-R_3-COO-$$

in which R$_2$ is a lower alkyl radical or a radical (R)$_3$Sn— where R is as defined above, p is 1 or 2, and R$_3$ is a saturated aliphatic, saturated alicyclic, or di- or trivalent aromatic hydrocarbon radical, a sulfonyloxy radical of the formula R$_1$—SO$_3$— in which R$_1$ is as defined above, a radical of the formula:

$$(O)P\begin{matrix}(OR_2)_2\\O-\end{matrix}$$

in which each R$_2$, which may be identical or different, is as defined above, or a radical of the formula:

$$(O)_2S\begin{matrix}OR_2\\O-\end{matrix}$$

in which R$_2$ is as defined above.

3. The storage-stable composition as defined by claim 1, wherein said at least one organostannic compound is tribenzyltin chloride, tribenzyltin fluoride, tributyltin chloride, tricyclohexyltin bromide, triisobutyltin chloride, trioctyltin bromide, triphenyltin chloride, tris(-paracarbomethoxyphenyl)tin chloride, tris(p-chlorophenyl)tin chloride, bis(2-carbomethoxyethyl)-propyltin chloride, butyldicyclohexyltin bromide, decyldimethyltin bromide, dibutylphenyltin chloride, dimethyloctyltin bromide, phenyldioctyltin bromide, diphenyloctyltin chloride, dodecyldiethyltin chloride, methoxytributyltin, methoxytrioxtyltin, butoxytributyltin, (n-octyl-thio)triethyltin, (tert-butylthio)triethyltin, dibutyldodecyltin laurate, bis(tributyltin) phthalate, dodecyldiethyltin acetate, bis(triethyltin) sulfate, dibutyl(dodecylthio)tin laurate, bis(dibutylmethoxytin) phthalate, triethyltin and tributyltin oxide, bis(tributyltin) sulfide, bis(triphenyltin) sulfide, tributyltin benzoate, tributyltin diethyl phosphate, tris(tributyltin) phosphate, lauryldiethyltin acetate, triethyltin laurate, or triethyl(isobutylthio)tin.

4. The storage-stable composition as defined by claim 1, said inert organic solvent coprising an ester, ketone, halocarbon, aromatic hydrocarbon, haloaromatic hydrocarbon or ether.

5. The storage-stable composition as defined by claim 1, said inert organic solvent comprising a hydrophilic organic solvent.

6. The storage-stable composition as defined by claim 1, said polyisocyanate comprising an aromatic, aliphatic or alicyclic diisocyanate, a biuret polyisocyanate, an isocyanurato polyisocyanate or an isocyanato adduct.

7. The storage-stable composition as defined in claim 1, comprising from $1 \cdot 10^{-4}$ to 5% by weight of said at least organostannic compound.

* * * * *